United States Patent
Zhang et al.

(10) Patent No.: US 12,037,494 B2
(45) Date of Patent: Jul. 16, 2024

(54) GUTTA-PERCHA CONTAINING CARBON NANOTUBES AND PREPARATION METHOD THEREFOR

(71) Applicants: Beijing University of Chemical Technology, Beijing (CN); Peking University Hospital of Stomatology, Beijing (CN)

(72) Inventors: Jichuan Zhang, Beijing (CN); Mengjie Dong, Beijing (CN); Li Liu, Beijing (CN); Xiubo Qu, Beijing (CN); Xiaoyan Wang, Beijing (CN); Chongyang Yuan, Beijing (CN); Yang Yu, Beijing (CN)

(73) Assignees: BEIJING UNIVERSITY OF CHEMICAL TECHNOLOGY, Beijing (CN); PEKING UNIVERSITY HOSPITAL OF STOMATOLOGY, Beijing (CN)

( * ) Notice: Subject to any disclaimer, the term of this patent is extended or adjusted under 35 U.S.C. 154(b) by 587 days.

(21) Appl. No.: 17/217,625

(22) Filed: Mar. 30, 2021

(65) Prior Publication Data

US 2021/0214531 A1   Jul. 15, 2021

Related U.S. Application Data

(63) Continuation of application No. PCT/CN2019/088815, filed on May 28, 2019.

(30) Foreign Application Priority Data

Jul. 25, 2018  (CN) .......................... 201810824157.4

(51) Int. Cl.
| | | |
|---|---|---|
| C08F 2/46 | (2006.01) | |
| C08F 2/50 | (2006.01) | |
| C08G 61/04 | (2006.01) | |
| C08K 3/04 | (2006.01) | |
| C08L 9/10 | (2006.01) | |
| C08K 3/22 | (2006.01) | |

(52) U.S. Cl.
CPC ............... *C08L 9/10* (2013.01); *C08K 3/041* (2017.05); *C08K 2003/2296* (2013.01); *C08K 2201/003* (2013.01); *C08K 2201/004* (2013.01); *C08K 2201/005* (2013.01)

(58) Field of Classification Search
CPC .... A61K 6/54; C08L 9/10; C08L 7/00; C08K 3/22; C08K 3/041; C08K 2201/003; C08K 2201/004; C08K 2201/005; C08K 2003/2296

USPC ................. 522/159, 158, 157, 150, 1; 520/1
See application file for complete search history.

(56) References Cited

U.S. PATENT DOCUMENTS 3,847,854 A * 11/1974 Canter et al. ............ C08K 5/01
524/378
2005/0282116 A1   12/2005 Kusano

FOREIGN PATENT DOCUMENTS

| CN | 106046441 A |   | 10/2016 |
|---|---|---|---|
| CN | 108192159   | * | 6/2018 |
| CN | 108192159 A |   | 6/2018 |
| CN | 109260027   | * | 1/2019 |
| CN | 109260027 A |   | 1/2019 |

OTHER PUBLICATIONS

Goh et al, Directional Alignment of carbon nanotubes in polymer matrices: Contemporary approaches and future advances, Oct. 12, 2013, Composites: Part A, 56, 103-126 (Year: 2013).*
Geng et al, CN 108192159 Machine Translation, Jun. 22, 2018 (Year: 2018).*
Zhang et al, CN 109260027 Machine Translation, Jan. 25, 2019 (Year: 2019).*
International Search Report issued in PCT/CN2019/088815 dated Aug. 27, 2019 with English translation, (4p).
Abbasi, Samaneh, et al., "Flow Induced Orientation of Multiwalled Carbon Nanotubes in Polycarbonate Nanocomposites: Rheology, Conductivity and Mechanical Properties", Elsevier Polymer Journal 51 (2010), (14p). journal homepage: www.elsevier.com/locate/polymer.
Goh, P.S., et al., "Directional Alignment of Carbon Nanotubes in Polymer Matrices: Contemporary Approaches and Future Advances", Elsevier Composites: Part 1 56 (2014), (24p). journal homepage: www.elsevier.com/locate/compositesa.

* cited by examiner

*Primary Examiner* — Jessica Whiteley
(74) *Attorney, Agent, or Firm* — Arch & Lake LLP

(57) ABSTRACT

The present disclosure relates to gutta-percha containing carbon nanotubes and a preparation method therefor. The gutta-percha is prepared by mixing a raw material, prepared from the following components of eucommia ulmoide gum, zinc oxide and carbon nanotubes, and extruding the mixed raw material. An orientation factor of the carbon nanotubes in the gutta-percha is greater than 10.8. The preparation method comprises: mixing the components according to dosages, and extruding a mixed product to prepare the gutta-percha containing carbon nanotubes.

17 Claims, 4 Drawing Sheets

GUTTA-PERCHA CONTAINING CARBON NANOTUBES AND PREPARATION METHOD THEREFOR

CROSS-REFERENCE TO RELATED APPLICATIONS

This application is based upon and claims the priority of PCT patent application No. PCT/CN2019/088815 filed on May 28, 2019 which claims priority to the Chinese patent application No. 201810824157.4 filed on Jul. 25, 2018, the entire content of both of which is hereby incorporated by reference herein for all purposes.

TECHNICAL FIELD

The present disclosure relates to the technical field of polymer materials and further relates to a gutta-percha containing carbon nanotubes and a preparation method therefor.

BACKGROUND

Root canal therapy is an effective means for treating dental pulp diseases and periapical diseases at present, while a gutta-percha point is a mostly applied filling material in the root canal therapy. However, because there are more complex anatomical structures, such as collateral branch root canals, in an apical segment of a root canal system, the filling material of the root canal is difficult to enter such irregular structure, and an ideal root canal filling effect cannot be thoroughly obtained clinically at present. Therefore, the gutta-percha point is required to have relatively high thermal conductivity and certain flowing property.

At present, a commercial gutta-percha is mainly composed of natural gutta-percha, zinc oxide, barium sulfate and the like, and the filling mass percentage of inorganic fillers, such as the zinc oxide, may be up to 70-80% typically, wherein a little quantity of the barium sulfate has a developing effect, and a large quantity of the zinc oxide acts as a main thermal conductive filler. According to analysis on components of different commercial gutta-perchas, it is discovered that increase of a thermal conductivity coefficient is positively relative to a filling quantity of the zinc oxide. However, while the thermal conductivity coefficient is increased, the fluidity of a material is severely influenced by the inorganic filler which are added largely. At this time, although the thermal conductivity is excellent, the inorganic filler is difficult to become a gutta-percha material with relatively good filling effect due to the limitation of the flowing property.

Through study, it is discovered that by adding carbon nanotubes with excellent thermal conductivity, the thermal conductivity and the flowing property are improved in a certain degree. However, because the carbon nanotubes are irregularly distributed in a rubber matrix, exertion of the thermal conductivity of the carbon nanotubes is limited, and the thermal conductivity and the flowing property still need further improvement.

Because heat transferred in an axial direction of each carbon nanotube is far greater than that transferred in a radial direction of each carbon nanotube, the thermal conductivity of a composite in an orientation direction is improved when the carbon nanotubes are in directional alignment in a rubber composite. However, it is not discovered that the thermal conductivity is enhanced through orientation of the filler in the preparation field of the gutta-percha materials.

SUMMARY

The present disclosure provides a thermal conductive gutta-percha and a preparation method therefor.

According to a first aspect of the present disclosure, a gutta-percha containing carbon nanotube is provided, including: a mix of raw materials, the raw materials further comprising: eucommia ulmoide gum, zinc oxide and carbon nanotubes, wherein an orientation factor of the carbon nanotubes in gutta-percha is greater than 10.8; wherein the gutta-percha containing carbon nanotube is prepared by mixing the raw materials and extruding the mixed raw materials.

According to a second aspect of the present disclosure, a preparation method of gutta-percha containing carbon nanotubes is provided, the method comprising: mixing raw materials according to dosages, and extruding a mixed product to prepare the gutta-percha containing carbon nanotubes, wherein the raw materials further comprise: eucommia ulmoide gum, zinc oxide and carbon nanotubes, wherein an orientation factor of the carbon nanotubes in gutta-percha is greater than 10.8.

DETAILED DESCRIPTION

The present disclosure is further described below in combination with examples.

The orientation factor is calculated according to polarization Raman spectroscopy, which is from a method for characterizing the orientation degree of the carbon nanotubes.

Reference will now be made in detail to specific implementations, examples of which are illustrated in the accompanying drawings. In the following detailed description, numerous non-limiting specific details are set forth in order to assist in understanding the subject matter presented herein. But it will be apparent to one of ordinary skill in the art that various alternatives may be used.

The terminology used in the present disclosure is for the purpose of describing exemplary examples only and is not intended to limit the present disclosure. As used in the present disclosure and the appended claims, the singular forms "a," "an" and "the" are intended to include the plural forms as well, unless the context clearly indicates otherwise. It shall also be understood that the terms "or" and "and/or" used herein are intended to signify and include any or all possible combinations of one or more of the associated listed items, unless the context clearly indicates otherwise.

Reference throughout this specification to "one embodiment," "an embodiment," "an example," "some embodiments," "some examples," or similar language means that a particular feature, structure, or characteristic described is included in at least one embodiment or example. Features, structures, elements, or characteristics described in connection with one or some embodiments are also applicable to other embodiments, unless expressly specified otherwise.

As used herein, the term "if" or "when" may be understood to mean "upon" or "in response to" depending on the context. These terms, if appear in a claim, may not indicate that the relevant limitations or features are conditional or optional.

Figure 1:
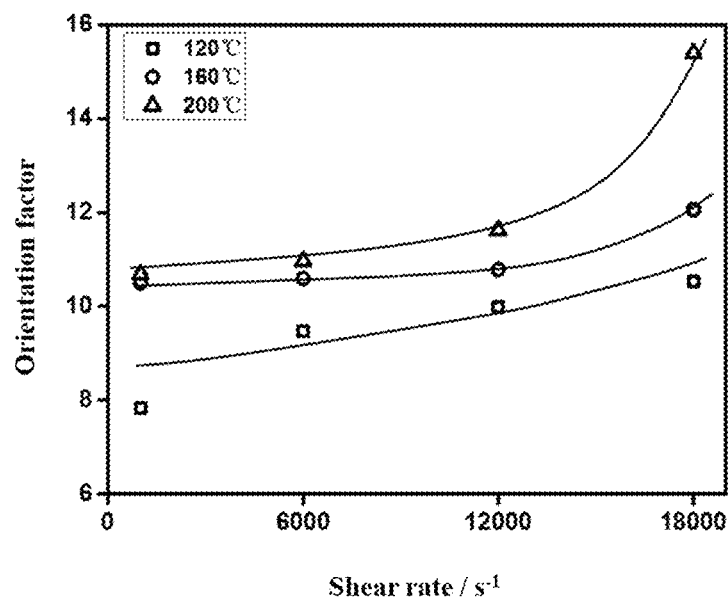
FIG. 1 is a relationship diagram for an orientation degree to a shear rate and a temperature according to an example of the present disclosure.

FIG. 1 shows that, at a same temperature, the larger the shear rate is, the higher the orientation degree is; and at a same shear rate, during low shearing, the influence of the temperature is relatively small, and during high shearing, the higher the temperature is, the higher the orientation degree is.

The orientation schematic diagrams in FIGS. 2A-2F are drawn according to a scanning electron micrograph for a clear surface orientation.

0 #is a sample without being oriented, long axes of the carbon nanotubes may be seen on the cross section of the sample, and distribution, perpendicular to the cross section, of the carbon nanotubes may also be seen. Whereas, for a 12 #sample subjected to shearing orientation, when wetting off is performed in the orientation direction, the long axes of the carbon nanotubes exist on seen cross sections substantially; and when wetting off is performed in a direction perpendicular to the orientation direction, all can be seen is dots formed by diameters of the carbon nanotubes substantially. Through comparison, a result that the carbon nanotubes are in directional alignment indeed after being subjected to the effect of the shearing force of the capillary rheometer may be obtained.

Figure 2A:
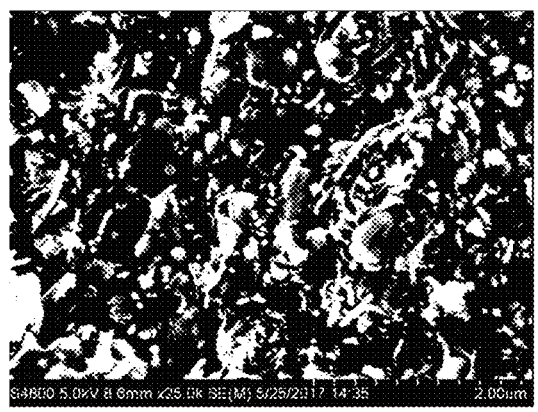
FIG. 2A is a scanning electron micrograph of a comparative example (0 #).
Figure 2B:
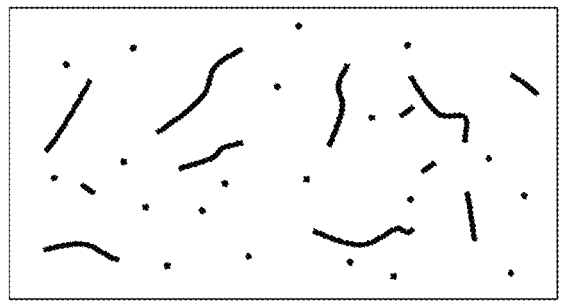
FIG. 2B is an orientation schematic diagram of the comparative example (0 #).

FIG. 2A shows the scanning electron micrograph according to the Comparative Example in the present disclosure. FIG. 2B is the orientation schematic diagrams of this Comparative Example. The sample of this Comparative Example is scanned and illustrated without being oriented.

Figure 2C:
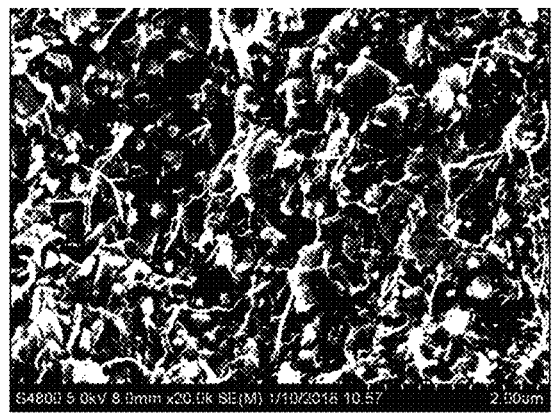
FIG. 2C is a scanning electron micrograph, parallel to the orientation direction, of an example of the present disclosure (12 #).
Figure 2D:
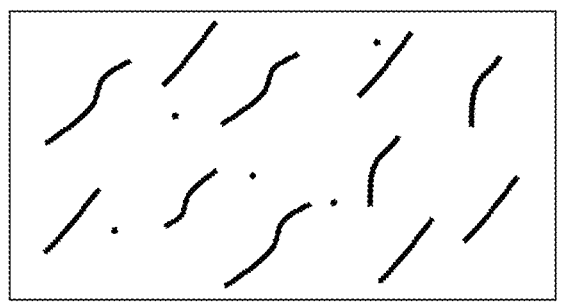
FIG. 2D is an orientation schematic diagram, parallel to the orientation direction, of an example of the present disclosure (12 #).

FIG. 2C shows the scanning electron micrograph, parallel to the orientation direction, according to Example 3 in the present disclosure. FIG. 2D is the orientation schematic diagrams, parallel to the orientation direction, of Example 3. The sample of this Example 3 is scanned and illustrated subjected to shearing orientation.

Figure 2E:
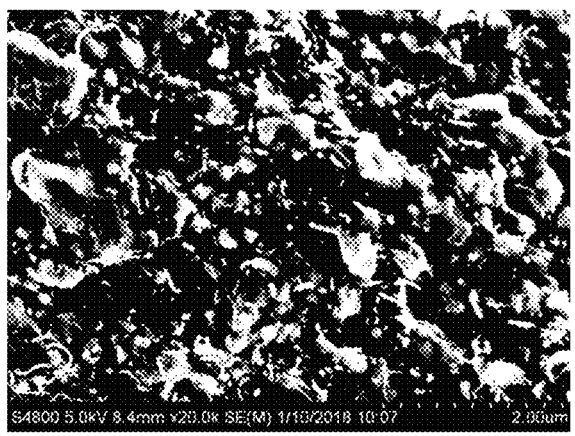
FIG. 2E is a scanning electron micrograph, perpendicular to the orientation direction, of an example of the present disclosure (12 #).
Figure 2F:
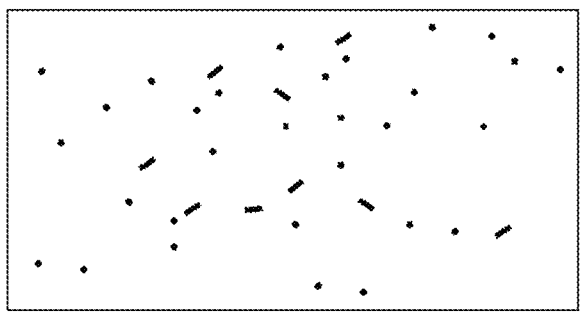
FIG. 2F is an orientation schematic diagram, perpendicular to the orientation direction, of an example of the present disclosure (12 #).

FIG. 2E shows the scanning electron micrograph, perpendicular to the orientation direction, according to Example 3 in the present disclosure. FIG. 2F is the orientation schematic diagrams, perpendicular to the orientation direction, of Example 3.

Figure 3:
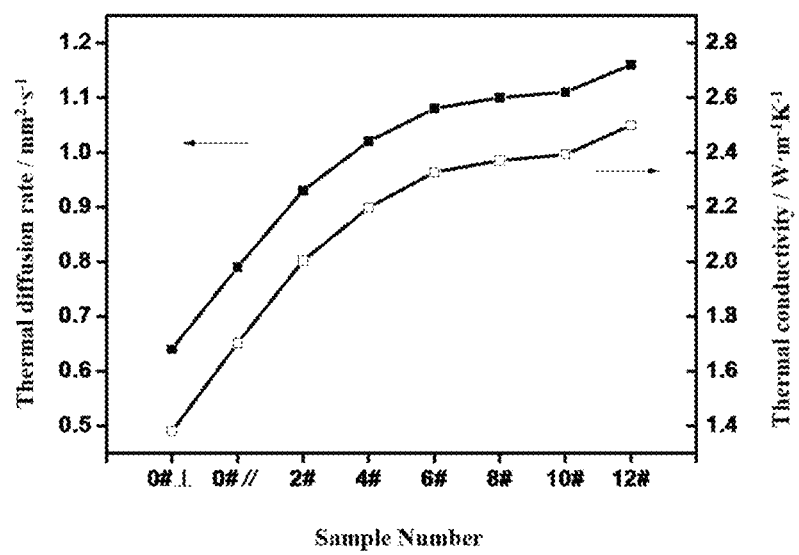
FIG. 3 is a change curve diagram of the thermal conductivity of different samples.
Figure 4:
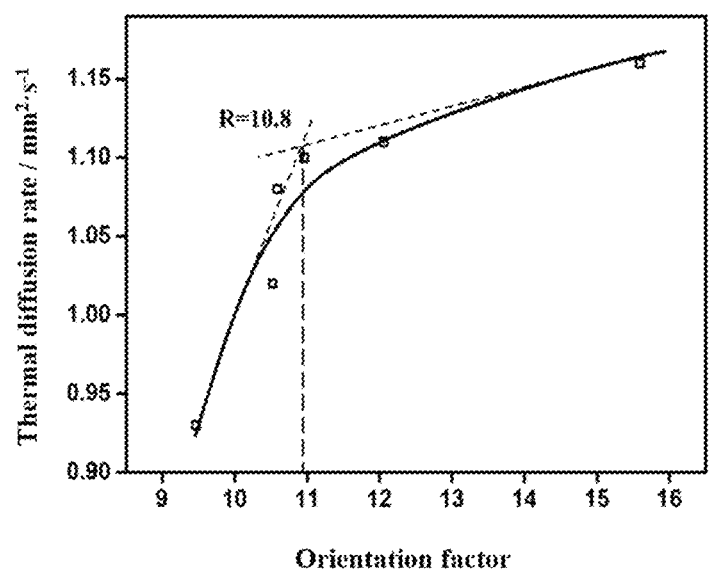
FIG. 4 is a change curve diagram of the thermal conductivity over the orientation degree.

FIG. 3 shows that as a shearing temperature and rate rise, the thermal conductivity is relatively rapidly improved at the beginning, and then an improvement rate of the thermal conductivity is slowed down gradually. (0 #represents the sample without being shorn, and 1 #-4 #correspond to 120° C. separately.)

Thermal conduction is positively relative to the orientation degree of the carbon nanotubes; and when the orientation factor R is about 10.8, a permeation threshold occurs, and a thermal conductive network structure is formed between the carbon nanotubes in the orientation direction and the zinc oxide substantially in a test. Subsequently, with increase of the orientation degree, the thermal conductivity is slowly improved.

Figure 5:
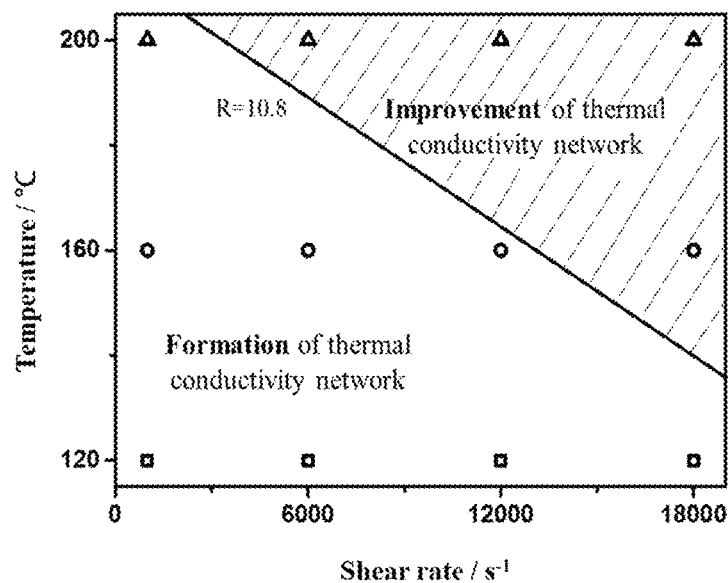
FIG. 5 is a phase diagram of a shearing temperature and a shear rate.

FIG. 5 may be used for directing an actual preparation process. In a lower-left corner range, the thermal conductivity may be improved obviously with increase in the shearing temperature and the shear rate; however, the temperature and the rate reach a portion at the upper-right corner after being increased to a certain degree, and the thermal conductivity would be slowly improved if the shearing temperature and the shear rate are continuously increased. The condition nearby a line of the orientation factor R=10.8 is a preferred condition, and the situation that energy waste is reduced while the thermal conductivity is improved is ensured.

Figure 6:
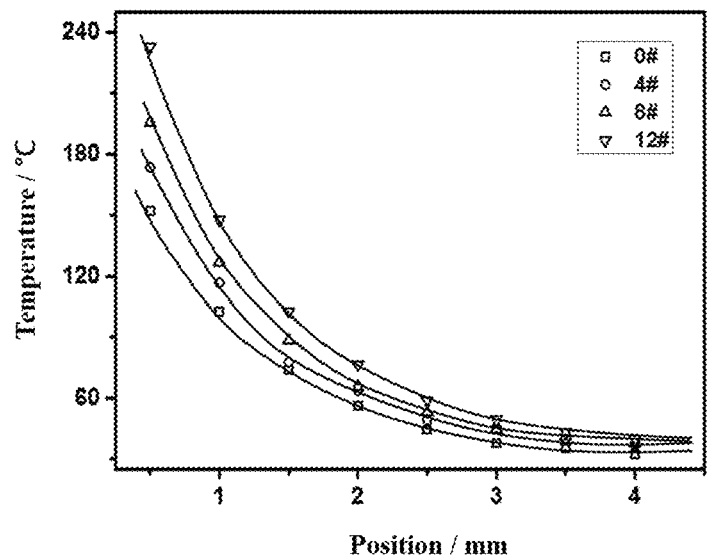
FIG. 6 is an infrared thermography testing diagram of examples of the present disclosure.

Seen from FIG. 6, a temperature of the sample subjected to orientation is higher than that of the 0 #sample after being oriented; and at a same position, the higher the shearing temperature is, the higher the temperature of the gutta-percha is, and the better the thermal conductivity is.

COMPARATIVE EXAMPLE

A temperature of a hot roller is set to be 75° C., the quantity of the eucommia ulmoide gum is 100 mass parts, the quantity of the zinc oxide is 400 mass parts, and the quantity of the carbon nanotube is 20 mass parts. After uniform mixing, a test is performed with the orientation factor being 4.85 (with a sample number 0 #); and if the carbon nanotubes are isotropic in the composite, the orientation factor should be 1, which shows that a small quantity of orientation of the carbon nanotubes also occurs due to the effect of the open mill in the mixing process. Thermal diffusion rates in a vertical direction and a parallel direction are tested to be 0.64 $mm^2/s$ and 0.79 $mm^2/s$ respectively, and this result shows that the composite is in a small quantity of orientation indeed when not being extruded by the capillary rheometer, and the thermal conductivity of the composite is anisotropic.

Example 1

A temperature of a hot roller is set to be 75° C., the quantity of the eucommia ulmoide gum is 100 mass parts, the quantity of the zinc oxide is 400 mass parts, and the quantity of the carbon nanotube is 20 mass parts. After uniform mixing, extrusion with the capillary rheometer is performed, wherein the extrusion temperature is 120° C., and the shear rate is 6000 $s^{-1}$ (with a corresponding number 2 #), the orientation factor of the carbon nanotubes in the composite is 9.46, which shows that the orientation degree is increased, and the thermal diffusion rate in a direction parallel to the orientation direction is 0.93 $mm^2/s$ and is increased by 17.8% compared to the thermal diffusion rate of the sample without being oriented in the parallel direction.

Example 2

A temperature of a hot roller is set to be 75° C., the quantity of the eucommia ulmoide gum is 100 mass parts, the quantity of the zinc oxide is 400 mass parts, and the quantity of the carbon nanotube is 20 mass parts. After uniform mixing, extrusion with the capillary rheometer is performed, wherein the extrusion temperature is 120° C., and the shear rate is 18000 s$^{-1}$ (with a corresponding number 4 #), the orientation factor of the carbon nanotubes in the composite is 10.52, which shows that the orientation degree is increased compared with the 0 #sample without being subjected to shearing orientation, and the thermal diffusion rate in a direction parallel to the orientation direction is 1.02 mm$^2$/s and is increased by 29.1% compared to the thermal diffusion rate of the sample without being oriented in the parallel direction.

Example 3

A temperature of a hot roller is set to be 75° C., the quantity of the eucommia ulmoide gum is 100 mass parts, the quantity of the zinc oxide is 400 mass parts, and the quantity of the carbon nanotube is 20 mass parts. After uniform mixing, extrusion with the capillary rheometer is performed, wherein the extrusion temperature is 200° C., and the shear rate is 18000 s$^{-1}$ (with a corresponding number 12 #), the orientation factor of the carbon nanotubes in the composite is 15.39, which shows that the orientation degree is increased compared with the 0 #sample without being subjected to shearing orientation, and the thermal diffusion rate in a direction parallel to the orientation direction is 1.16 mm$^2$/s and is increased by 46.8% compared to the thermal diffusion rate of the sample without being oriented in the parallel direction.

Example 4

A temperature of a hot roller is set to be 75° C., the quantity of the eucommia ulmoide gum is 100 mass parts, the quantity of the zinc oxide is 250 mass parts, and the quantity of the carbon nanotube is 10 mass parts. After uniform mixing, extrusion with the capillary rheometer is performed, wherein the extrusion temperature is 200° C., and the shear rate is 18000 s$^{-1}$, the orientation factor of the carbon nanotubes in the composite is 16.20, and the thermal diffusion rate in a direction parallel to the orientation direction is 0.89 mm$^2$/s, which states that the thermal conductivity of the sample after being filled with 10 mass parts of the carbon nanotube and being subjected to shearing orientation is better than that of the sample after being filled with 10 mass parts of the carbon nanotube and without being subjected to orientation.

Example 5

A temperature of a hot roller is set to be 75° C., the quantity of the eucommia ulmoide gum is 100 mass parts, the quantity of the zinc oxide is 500 mass parts, and the quantity of the carbon nanotube is 50 mass parts. After uniform mixing, extrusion with the capillary rheometer is performed, wherein the extrusion temperature is 200° C., and the shear rate is 18000 s$^{-1}$, the orientation factor of the carbon nanotubes in the composite is 14.96, which shows that the orientation degree is increased, and the thermal diffusion rate in a direction parallel to the orientation direction is 1.43 mm$^2$/s.

Example 6

A temperature of a hot roller is set to be 75° C., the quantity of the eucommia ulmoide gum is 100 mass parts, the quantity of the zinc oxide is 400 mass parts, and the quantity of the carbon nanotube is 20 mass parts. After simple mixing, the materials are put in a twin-screw extruder with the extrusion temperature being 120° C. and the rotating speed of the screws being 20 revolutions per minute, the orientation factor of the carbon nanotubes in the composite is 11.82, which shows that the orientation degree is increased, and the thermal diffusion rate in a direction parallel to the orientation direction is 1.05 mm$^2$/s.

The present disclosure provides a gutta-percha containing carbon nanotube.

Eucommia ulmoide gum, zinc oxide and carbon nanotubes.

An orientation factor of the carbon nanotubes in the gutta-percha is greater than 10.8.

The gutta-percha is prepared by mixing a raw material, prepared from the following components, and extruding the mixed raw material.

The components in parts by weight are as follows:
Eucommia ulmoide gum 100 parts;
Zinc oxide 250-500 parts, preferably, 300-450 parts;
Carbon nanotube 1-50 parts, preferably, 20-40 parts;
wherein preferably:
a dosage ratio of the zinc oxide to the carbon nanotubes is (5-500) to 1, and
a dosage ratio of the zinc oxide to the carbon nanotubes is (10-20) to 1.

A particle size range of the zinc oxide is 100-400 nm.
A diameter of each carbon nanotube is about 20-30 nm, and a length-diameter ratio is greater than 50.

Conventional auxiliaries, i.e., a plasticizer, a pigment, a developer and the like, such as paraffin oil and barium sulfate, may be added into the gutta-percha of the present disclosure according to actual conditions, and the dosages of the conventional auxiliaries are also conventional and determined by those skilled in the art according to the actual conditions.

The present disclosure also provides a preparation method of the gutta-percha containing carbon nanotubes.

The preparation method comprises: mixing the components according to the dosages, and extruding a mixed product to prepare the thermal conductive gutta-percha.

A mixing device may employ an existing mixing device, and mixing process conditions are conventional process conditions of the eucommia ulmoide gum and, in the present disclosure, may be preferably as follows: a mixing temperature is 60-80° C., and a time is 5-10 min until uniform mixing.

An extrusion temperature range is 120-200° C.

Extrusion may employ an existing extrusion device, and a preferred extrusion temperature range of an extruder is 80-160° C. Preferably, extrusion is performed on a twin-screw extruder, a length-diameter ratio of each screw is 25 to 1, the diameter of each screw is 25 mm, and a rotating speed of each screw is 20 revolutions per minute.

In consideration of a required shape of a subsequently prepared gutta-percha point, subsequent preparation is facilitated by filament-forming extrusion with a shearing method; a temperature and a shear rate of a capillary rheometer are both controllable; and preferably, a method of shearing orientation of the capillary rheometer is adopted, so that a temperature and shear rate conditions capable of obtaining a relatively good orientation are explored. Preferably: an extrusion temperature range of the capillary rheometer is 120-200° C., and a range of the shear rate is 1000 s-1-18000 s-1.

In combination with the shape of the gutta-percha point, if the carbon nanotubes can be oriented in a long axis direction of the gutta-percha point, positive impacts in two aspects may be generated, wherein one positive impact is as follows: the thermal conductivity is improved, and a tip is easily softened with heating; and the other positive impact is as follows: entanglement between the carbon nanotubes may further be reduced due to the effect of orientation, and the situation that the carbon nanotubes flow into collateral branch root canals is more facilitated. Through extrusion with the capillary rheometer, the situation that the gutta-percha material is further processed and molded under the condition of keeping the orientation of the carbon nanotubes is facilitated.

In the present disclosure, a natural gutta-percha-zinc oxide-carbon nanotube composite (with the mass ratio of 100 to 400 to 20) is prepared on a hot-roller open mill at 75° C. for the first time; then, the composite is shorn and extruded (numbers in an experiment: 0 #representing the composite without being shorn, 1 #-4 #corresponding to four shear rates at 120° C. respectively, as well as 4 #-8 #and 9 #-12 #corresponding to four shear rates at 160° C. and 200° C. from smallest to largest respectively) by the capillary rheometer under the conditions of different temperature ranges (120° C., 160° C. and 200° C.) and different shear rates (1000 s-1, 6000 s-1, 12000 s-1 and 18000 s-1), and the carbon nanotubes are oriented by using a shear force of the capillary rheometer; and then, a microstructure change and the macro-performance of the material are characterized.

The characterization means mainly comprises: 1. polarization Raman spectroscopy semi-quantitation characterizes an orientation degree of the carbon nanotubes, the orientation degree is expressed by an orientation factor, and the higher the orientation factor is, the higher the orientation degree of the carbon nanotubes is; 2. the thermal conductivity (GB/T 22588-2008) of the orientation direction is determined with a laser flash method; and 3. a temperature change of the gutta-percha point in the in vitro filling process is analyzed with infrared thermography.

Experiment results show that through the shearing effect of the capillary rheometer, the orientation degree of the capillary rheometers in the composite is increased obviously, and the orientation factor (which is a ratio of polarization Raman spectroscopy peak intensities parallel to and perpendicular to an orientation direction and used for characterizing the orientation degree, wherein the larger the ratio is, the higher the orientation degree is) becomes large as the shearing temperature rises and also as the shear rate is increased. Through a thermal conductivity test, a thermal diffusion rate after orientation is increased obviously. Infrared thermography results show that a temperature of the gutta-percha after being oriented is higher than that of the gutta-percha without being oriented, which shows that the thermal conductivity of the carbon nanotubes after being oriented is strengthened.

Polarization Raman spectroscopy results show that, when the material is not subjected to shearing orientation, the orientation factor is 4.85; after the shearing effect, the orientation factor is maximally 15.39; and the thermal diffusion rate maximally rises from 0.64 mm2/s, when orientation is not performed, to 1.16 mm2/s.

The invention claimed is:

1. A gutta-percha containing carbon nanotube, comprising:
   a mix of raw materials comprising: eucommia ulmoide gum, zinc oxide and carbon nanotubes, wherein an orientation factor of the carbon nanotubes in gutta-percha is greater than 10.8,
   wherein an orientation degree of the carbon nanotubes is positively related to the orientation factor.

2. The gutta-percha containing carbon nanotube according to claim 1, wherein the raw materials comprise:
   100 parts of eucommia ulmoide gum;
   250-500 parts of zinc oxide; and
   1-50 parts of carbon nanotubes, wherein the parts are measured by weight.

3. The gutta-percha containing carbon nanotube according to claim 1, wherein the raw materials comprise:
   100 parts of eucommia ulmoide gum;
   300-450 parts of zinc oxide; and
   20-40 parts of carbon nanotubes; wherein the parts are measured by weight.

4. The gutta-percha containing carbon nanotube according to claim 2, wherein
   a dosage ratio of the zinc oxide to the carbon nanotubes is among a range of 5:1 to 500:1.

5. The gutta-percha containing carbon nanotube according to claim 4, wherein
   a dosage ratio of the zinc oxide to the carbon nanotubes is among a range of 10:1 to 20:1.

6. The gutta-percha containing carbon nanotube according to claim 2, wherein
   a particle size range of the zinc oxide is 100-400 nm.

7. The gutta-percha containing carbon nanotube according to claim 2, wherein
   a diameter of each carbon nanotube is 20-30 nm, and a length-diameter ratio is greater than 50:1.

8. A preparation method of gutta-percha containing carbon nanotubes, comprising:
   mixing raw materials according to dosages, and extruding a mixed product to prepare the gutta-percha containing carbon nanotubes, wherein the raw materials further comprise:
   eucommia ulmoide gum, zinc oxide and carbon nanotubes, wherein an orientation factor of the carbon nanotubes in gutta-percha is greater than 10.8; and
   wherein an orientation degree of the carbon nanotubes is positively related to the orientation factor.

9. The preparation method of claim 8, wherein
   an extrusion temperature range is 70-200° C.

10. The preparation method of claim 8, wherein
    the raw materials are mixed according to the dosages, and extruded by a capillary rheometer to prepare thermal conductive gutta-percha; and
    an extrusion temperature of the capillary rheometer is 120-200° C., and a shear rate is 1000 s-1-18000 s-1.

11. A gutta-percha containing carbon nanotube, comprising:
    a mix of raw materials comprising: eucommia ulmoide gum, zinc oxide and carbon nanotubes, wherein an orientation factor of the carbon nanotubes in gutta-percha is greater than 10.8;
    wherein a permeation threshold occurs when the orientation factor of the nanotubes in the gutta-percha is about 10.8.

12. The gutta-percha containing carbon nanotube according to claim 11, wherein the raw materials comprise:
    100 parts of eucommia ulmoide gum;
    250-500 parts of zinc oxide; and
    1-50 parts of carbon nanotubes, wherein the parts are measured by weight.

13. The gutta-percha containing carbon nanotube according to claim 11, wherein the raw materials comprise:
   100 parts of eucommia ulmoide gum;
   300-450 parts of zinc oxide; and
   20-40 parts of carbon nanotubes; wherein the parts are measured by weight.

14. The gutta-percha containing carbon nanotube according to claim 12, wherein
   a dosage ratio of the zinc oxide to the carbon nanotubes is among a range of 5:1 to 500:1.

15. The gutta-percha containing carbon nanotube according to claim 14, wherein
   a dosage ratio of the zinc oxide to the carbon nanotubes is among a range of 10:1 to 20:1.

16. The gutta-percha containing carbon nanotube according to claim 12, wherein
   a particle size range of the zinc oxide is 100-400 nm.

17. The gutta-percha containing carbon nanotube according to claim 12, wherein
   a diameter of each carbon nanotube is 20-30 nm, and a length-diameter ratio is greater than 50:1.

* * * * *